United States Patent [19]

Streck et al.

[11] Patent Number: 5,306,856
[45] Date of Patent: Apr. 26, 1994

[54] METHOD OF MANUFACTURING METHYLIDENE-GROUP-CONTAINING α, ω-UNSATURATED OLIGOMERS FROM α, ω-DIOLEFINS IN THE PRESENCE OF ORGANOALUMINUM COMPOUNDS AS CATALYSTS

[75] Inventors: Roland Streck; Jaroslaw Monkiewicz, both of Marl; Hans G. Wey, Muelheim/Ruhr, all of Fed. Rep. of Germany

[73] Assignee: Huels Aktiengesellschaft, Marl, Fed. Rep. of Germany

[21] Appl. No.: 897,388

[22] Filed: Jun. 12, 1992

[30] Foreign Application Priority Data

Jun. 12, 1991 [DE] Fed. Rep. of Germany ....... 4119332

[51] Int. Cl.$^5$ ................................................. C07C 2/46
[52] U.S. Cl. ................................. 585/508; 585/506; 585/507; 585/511
[58] Field of Search ............... 585/506, 507, 508, 512, 585/511

[56] References Cited

U.S. PATENT DOCUMENTS

| | | | |
|---|---|---|---|
| 3,320,168 | 5/1967 | Suzuki | 585/506 |
| 3,356,704 | 12/1967 | Marcus | 585/317 |
| 3,391,209 | 7/1968 | Marcus | 585/317 |
| 3,429,940 | 2/1969 | Wadsworth | 585/368 |
| 3,480,685 | 11/1969 | Feldman et al. | 585/511 |
| 3,754,048 | 8/1973 | Wu et al. | 502/117 |
| 3,804,913 | 4/1974 | Goodwin | 585/368 |
| 4,148,983 | 4/1979 | Throckmorton | 502/117 |
| 4,954,125 | 9/1990 | Ono et al. | 585/508 |
| 5,113,033 | 5/1992 | Myers et al. | 585/506 |

*Primary Examiner*—Anthony MacFarlane
*Attorney, Agent, or Firm*—Oblon, Spivak, McClelland, Maier & Neustadt

[57] ABSTRACT

A method of manufacturing methylidene-group-containing α,ω-unsaturated oligomers from α,ω-diolefins in the presence of a catalytic amount of organoaluminum compounds, wherein the α,ω-diolefins are reacted in the liquid phase, at 150°–350° C., and the organoaluminum compounds have formula $AlX_3$ or $AlX_2H$, where X represents an aliphatic, alicyclic, or aromatic hydrocarbon group with 1–30 C atoms. The higher molecular weight hydrocarbons manufactured according to this method are substantially linear oligomers which contain reactive double bonds.

9 Claims, No Drawings

METHOD OF MANUFACTURING METHYLIDENE-GROUP-CONTAINING α,ω-UNSATURATED OLIGOMERS FROM α,ω-DIOLEFINS IN THE PRESENCE OF ORGANOALUMINUM COMPOUNDS AS CATALYSTS

BACKGROUND OF THE INVENTION

1. Field of the Invention

The invention relates to a method of manufacturing methylidene-group-containing α,ω-unsaturated oligomers from α,ω-diolefins in the presence of organoaluminum compounds as catalysts, and to compositions produced by this method.

2. Discussion of the Background

It is known that α-olefins when heated with catalytic amounts of trialkylaluminums or dialkylaluminum hydrides react to form mixtures containing a predominance of β-branched α-olefins having twice the number of carbon atoms compared with the initial olefin. For example, the main product in the dimerization of propene is 2-methyl-1-pentene and the main product in the dimerization of 1-butene is 2-ethyl-1-hexene (see German Pats. 878,560 and 925,291; also 629 *Liebigs Ann. Chem.* 121–166 (1960)).

When the above reaction is employed with hydrocarbons having two terminal vinyl groups (α,ω-diolefins), the principal products isolated are cyclic. Thus, butadiene results in a mixture of methyldimethylenecyclopentanes (U.S. Pat. Nos. 3,356,704 and 3,391,209; 1969 *J. Org. Chem.*, 34, 1931–1935), and 1,5-hexadiene and 1,6-heptadiene are cyclized to methylenecyclopentane and methylenecyclohexane, respectively (70 *Angew. Chem.* 862–863 (1967); 1976 *Tetrahed. Lett.*, 1257–1258). The same observation was made in studies of bis-hydroalumination of α,ω-diolefins (28 *J. Org. Chem.* 3237–3238 (1963)). There was only parenthetic mention of the production of small amounts of higher homologs from the α,ω-diolefins, which was not the stated purpose of the synthesis. Methods of manufacturing polymeric hydrocarbons starting with α,ω-diolefins and using organoaluminum compounds as catalysts are not known.

SUMMARY OF THE INVENTION

Accordingly, it is an object of this invention to provide method of manufacturing linear high molecular weight hydrocarbons having reactive double bonds, from α,ω-diolefins.

This object is achieved by reacting α,ω-diolefins having the general formula:

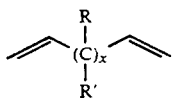

in a liquid phase, at 150°–350° C., in the presence of catalytically active amounts of organoaluminum compounds having the general formula $AlX_3$ or $AlX_2H$, where R and $R^1$ each independently represent hydrogen or an alkyl, aryl, aralkyl or cycloalkyl group;

x is 1 or a number betwen 3 and 25; and

X is any aliphatic, alicyclic, or aromatic hydrocarbon group containing 1–30 carbon atoms, preferably 2–20 carbon atoms.

The resulting methylidene-group-containing α,ω-unsaturated oligomer has the general formula:

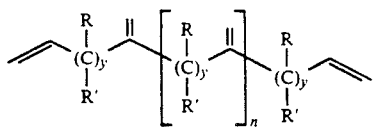

where R, R', and x are defined above;

n is a number between 0 and 99;

y = x or x+2; and $\Sigma C_k = (x+4)(n+2) - (n+1)$ is the expression for the sum of the C-atoms in the chain.

DETAILED DESCRIPTION OF THE PREFERRED EMBODIMENTS

Typical α,ω-diolefins suitable for synthesizing the inventive oligomers are: 1,4-pentadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, 1,14-pentadecadiene, 1,15-hexadecadiene, 1,16-heptadecadiene, 1,17-octadecadiene, 1,18-nonadecadiene, 1,19-eicosadiene, 1,3- and 1,4-divinylcyclohexane, 1,3,5-trivinylcyclohexane, etc.; and derivatives of these which are substituted, other than on the double bonds, by alkyl, cycloalkyl, aryl, or aralkyl groups having 1–30 C atoms. Higher unsaturated hydrocarbons can be components of the chain, in addition to the above-named α,ω-diolefins; only the terminal vinyl groups enter into reaction under the above-described reaction conditions. Although such a compound is regarded as a tri-, tetra-, or multiolefin on the basis of the total number of double bonds it contains, in practice it behaves like a bifunctional unit. Examples of such olefins which might be mentioned are: 1,4,7-octatriene, 1,4,7- and 1,4,8-nonatriene, 1,4,9- and 1,5,9-decatriene, 1,4,10- and 1,5,10-undecatriene; 1,4,7,11-, 1,5,8,11- 1,4,8,11- and 1,5,7,11-dodecatetraene; 1,5,9,13-tetradecatetraene, 4-methyl-1,4,7-octatriene, 5,6-dimethyl-1,5,9-decatriene, 4,4-dimethyl-6,7-diethyl-1,5,12-tridecatriene, etc.

As catalysts one may use all organoaluminum compounds having formulas corresponding to $AlX_3$ or $AlX_2H$, where X represents any aliphatic, alicyclic, or aromatic hydrocarbon group containing 1–30 C atoms, preferably 2–20 C atoms. Examples of such catalysts are: trimethylaluminum, triethylaluminum, tripropylaluminum, triisopropylaluminum, tri-n-butylaluminum, tri-sec-butylaluminum, tri-n-pentylaluminum, triisobutylaluminum, tri-2-methylpentylaluminum, tri-n-hexylaluminum, trineohexylaluminum, tri-n-heptylaluminum, tri-n-octylaluminum, tri-2-ethylhexylaluminum, tricyclopentylaluminum, tricyclohexylaluminum, tri(ethylcyclohexenyl)aluminum, triphenylaluminum, tri(phenylethyl)aluminum, trinaphthylaluminum; also mixtures of higher trialkylaluminums produced by the so-called "synthetic reaction" ("Aufbau-Reaktion") by addition of ethylene to lower aluminum trialkyls; and also dimethylaluminum hydride, diethylaluminum hydride, dipropylaluminum hydride, di-n-butylaluminum hydride, diisobutylaluminum hydride, dipentylaluminum hydride, dihexylaluminum hydride, diheptylaluminum hydride, dioctylaluminum hydride, dinonylaluminum hydride, didecylaluminum hydride; etc.

The catalytically active compounds may be added individually or as mixtures. They may be prepared in the presence of the unsaturated hydrocarbons to be reacted by starting with catalytically inactive precursors of the catalysts. For example, triethylaluminum may be prepared from diethylaluminum chloride and metallic sodium, or from sodium tetraethylaluminum.

The concentration of the catalyst may vary within wide limits. In practice, one generally keeps the concentration between 0.1 and 10 mol % (based on the amount of material charged). Particularly preferred is a catalyst concentration of 0.1–5 mol %.

The reaction temperature is between 150° and 350° C., preferably between 180° and 250° C. The reaction time decreases with increasing catalyst concentration. The reaction time is typically within the range of 48 hr to 5 min. The suitable combination of the catalyst concentration, reaction temperature, and reaction time should be selected such that the formation of undesired byproducts by isomerization of the terminal vinyl groups or the methylidene groups is substantially suppressed. One skilled in the art can readily accomplish this with a few orienting experiments and interpolation or extrapolation.

Reactions carried out discontinuously in reactors (e.g. autoclaves or stirred heated reactors) require relatively long reaction times. If the reaction is carried out in a continuous-flow reactor having a low operating volume and a narrow residence time spectrum, such as a tubular flow reactor, reaction times in the range of 1 hr to a few minutes can be achieved.

Continuous-flow reactors are preferred when the reaction involves high reaction temperatures because under such conditions there is a greater tendency for irreversible degradation of the catalyst wherewith aluminum, aluminum carbide, etc. are formed.

Pressurization may be necessary if it is desired to keep the reactants in the liquid phase. Thus, it is advantageous to operate under a pressure automatically adjusted to the vapor pressure of the reactants at the desired operating temperature. In the range of possible reaction temperatures of 150°–350° C., the pressures developed may be, accordingly, 0.01–200 bar, depending on the volatility of the given monomers.

The reaction may be carried out in the presence or absence of an inert solvent. If it is desired to lower the viscosity, then it may be advantageous to employ a solvent, which also makes material feed easier, and obviates problems in separation and recycling associated with reactions carried out in the absence of a solvent.

If a solvent is used, it should be a dry saturated or dry aromatic hydrocarbon. Among the solvents which may be used are: n-butane, pentane and its isomers, hexane and its isomers, heptane and its isomers, octane and its isomers, nonane and its isomers, decane and its isomers, and so forth; further, cyclopentane, methylcyclopentane, dimethylcyclopentane, cyclohexane, methylcyclohexane, ethylcyclohexane, dimethylcyclohexane, cyclooctane, methylcyclooctane, dimethylcyclooctane, ethylcyclooctane, isopropylcyclohexane, trimethylcyclododecane, benzene, toluene, o-, p-, and m-cresol, cumene, ethylbenzene, dodecylbenzene (mixture of isomers), petroleum ether, ligroin, kerosene and similar petroleum fractions, paraffin oil, tetralin, decalin, mono- and dibenzyltoluene, and biphenyl.

One may achieve independent regulation of molecular weight by addition of monofunctional olefins such as $\alpha$-olefins. These olefins may have saturated end groups which are not subject to further oligomerization. However, if this method of molecular weight regulation is used a certain amount of unavoidable homodimers of the monoolefins employed is formed. However, this is of only secondary significance, because these dimers can be easily removed from the reaction mixture, and there are useful applications for these substances. The presence of hydrogen during the oligomerization, at 10–250 bar, will also lead to products of reduced molecular weight.

The monoolefins which may be used for molecular weight regulation are basically any of the unsaturated hydrocarbons having a vinyl group and capable of being dimerized with the aid of trialkylaluminums or dialkylaluminum hydrides, i.e. any linear $\alpha$-olefin not branched at the double bond and having 3–30 C atoms; e.g., propene, 1-butene, 1-pentene, 3-methyl-1-butene, 1-hexene, 3-methyl-1-pentene, 4-methyl-1-pentene, 3,3-dimethyl-1-butene, 1-heptene, 3-methyl-1-hexene, 4-methyl-1-hexene, 5-methyl-1-hexene, 3,4-dimethyl-1-pentene, 3,3-dimethyl-1-pentene, 1-octene, 3-methyl-1-heptene, 4-methyl-1-heptene, 5-methyl-1-heptene, 6-methyl-1-heptene, 3,3-dimethyl-1-hexene, 3,4-dimethyl-1-hexene, 4,4-dimethyl-1-hexene, 3,5-dimethyl-1-hexene, 5,5-dimethyl-1-hexene, 4,5-dimethyl-1-hexene, 3-ethyl-1-hexene, 4-ethyl-1-hexene, 3,3,4-trimethyl-1-pentene, 3,4,4-trimethyl-1-pentene, 1-nonene, 3-methyl-1-octene, 4-methyl-1-octene, 5-methyl-1-octene, 6-methyl-1-octene, 7-methyl-1-octene, and so forth. Also vinyl-group-bearing cyclic hydrocarbons may be used, e.g., vinylcyclopentane, vinylcyclohexane, allylcyclopentane, allylcyclohexane, 1-butenylcyclohexane, 1-pentenylcycloheptane, 1-hexenylcyclooctane, 1-octenylcycloundecane, styrene, allylbenzene, 1-undecylnaphthalene, vinylanthracenes, etc.

It is also possible to use, instead of the $\alpha$-olefins, multiply-unsaturated hydrocarbons having a terminal unsubstituted double bond and one or more interior and/or substituted double bonds. An example of such an only partially reacting diolefin is 4-vinylcyclohexene.

Surprisingly, high polymers do not form at all, but the reaction products remain confined to the oligomeric molecular weight range. Accordingly, one must assume that there is a breakdown mechanism which was not predicted at first.

As seen from the Examples, according to the invention under the given conditions, generally more than 70% of the products have a degree of oligomerization m in the range 3–20.

The inventive oligomers may find use as valuable starting materials in the areas of coatings and adhesives, e.g. after hydrocyanization and hydroformylation and further oxidation or hydrogenation.

Other features of the invention will become apparent in the course of the following description of exemplary embodiments which are given for illustration of the invention and are not intended to be limiting thereof.

EXAMPLES 1–14

In a steel autoclave purged with nitrogen, the reactions of the given $\alpha,\omega$-diolefins and $\alpha,\omega$-triolefins were carried out in the presence of a catalyst and possibly a solvent, at the given reaction temperatures and reaction times, until the described products were obtained. Then the mixture was cooled, and methanol was added, followed by addition of NaOH solution of strength 5%. Then the mixture was shaken and the aqueous layer was separated, the organic layer was washed neutral with distilled water and dried over sodium sulfate. The solvent and residual monomer were removed by distillation at atmospheric pressure and the dimers were removed by distillation in vacuum. The product which remained was characterized by gel permeation chromatography and determination of the iodine number. All of the other data on the starting materials, end products, and reaction conditions are provided in Table 1.

EXAMPLES 15–21

The procedure was initially the same as in Examples 1–14, using the same apparatus. After a stated reaction time II. the apparatus was filled with hydrogen to a pressure of 150 bar. Then the reaction was continued until the respective end product was obtained. The subsequent refinement of the mixture and characterization of the product were as in Examples 1–14. All other data on starting products, end products, and reaction conditions are provided in Table 2.

TABLE 1

| Example Number | α, ω Diolefin | Amount (mol) | Catalyst | Amount (mol) | Solvent | Amount (gram) |
|---|---|---|---|---|---|---|
| 1 | 1,4-Pentadiene | 2.91 | Diisobutylaluminum hydride | 0.12 | Cyclohexane | 198 |
| 2 | 1,7-Octadiene | 11.4 | Diisobutylaluminum hydride | 0.46 | — | — |
| 3 | " | 7.45 | Diisobutylaluminum hydride | 0.3 | — | — |
| 4 | " | 5.8 | Diisobutylaluminum hydride | 0.2 | — | — |
| 5 | " | 3.4 | Diisobutylaluminum hydride | 0.14 | — | — |
| 6 | " | 10.0 | Triisobutylaluminum | 0.4 | — | — |
| 7 | " | 13.9 | Diisobutylaluminum hydride | 0.4 | Cyclohexane | 778 |
| 8 | " | 3.3 | Diisobutylaluminum hydride | 0.13 | Hexane | 308 |
| 9 | 1,9-Decadiene | 4.3 | Diisobutylaluminum hydride | 0.17 | — | — |
| 10 | " | 2.2 | Diisobutylaluminum hydride | 0.09 | Cyclohexane | 311 |
| 11 | 1,11-Dodecadiene | 1.0 | Diisobutylaluminum hydride | 0.02 | — | — |
| 12 | " | 0.5 | Diisobutylaluminum hydride | 0.01 | Decahydro-naphthalene | 332 |
| 13 | 1,4,9-Decatriene | 0.49 | Diisobutylaluminum hydride | 0.025 | — | — |
| 14 | " | 14.12 | Diisobutylaluminum hydride | 0.7 | — | — |

| Example Number | Reaction Time (hr) | Reaction Temperature (°C.) | Raw Yield[1] (%) | $M_n$ | $M_w$ | Iodine Number |
|---|---|---|---|---|---|---|
| 1 | 1.5 | 200 | 37 | 199 | 242 | 310 |
| 2 | 0.16 | 200 | 46 | 516 | 540 | 265 |
| 3 | 0.5 | 200 | 66 | 797 | 1168 | 255 |
| 4 | 4 | 200 | 81 | 930 | 1819 | 238 |
| 5 | 4 | 200 | 77 | 619 | 1177 | 227 |
| 6 | 2 | 200 | 70 | 509 | 627 | 267 |
| 7 | 2.0 | 200 | 84 | 698 | 917 | 243 |
| 8 | 1.5 | 200 | 78 | 659 | 929 | 254 |
| 9 | 1.0 | 200 | 75 | 710 | 1012 | 222 |
| 10 | 1.0 | 200 | 53 | 533 | 676 | 225 |
| 11 | 4 | 180 | 87 | 660 | 837 | 193 |
| 12 | 20 | 184 | 85 | 610 | 835 | 198 |
| 13 | 10.0 | 163 | 63 | 528 | 560 | 292 |
| 14 | 4.0 | 220 | 56 | 439 | 479 | 346 |

[1] based on the molar amount of the diolefin charged, prior to distillation

TABLE 2

| Example Number | α, ω Diolefin | Amount (mol) | Catalyst | Amount (mol) | Solvent | Amount (gram) |
|---|---|---|---|---|---|---|
| 15 | 1,7-Octadiene | 9.1 | Diisobutylaluminum hydride | 0.36 | — | — |
| 16 | " | 20.0 | Diisobutylaluminum hydride | 0.82 | — | — |
| 17 | " | 10.0 | Diisobutylaluminum hydride | 0.6 | Cyclohexane | 1167 |
| 18 | " | 10.0 | Diisobutylaluminum hydride | 0.6 | " | 1167 |
| 19 | 1,9-Decadiene | 8.0 | Diisobutylaluminum hydride | 0.48 | " | 535 |
| 20 | 1,4,9-Decatriene | 1.97 | Diisobutylaluminum | 0.10 | — | — |

TABLE 2-continued

| | | | | | | |
|---|---|---|---|---|---|---|
| 21 | 1,13-Tetradecadiene | 0.93 | hydride Diisobutylaluminum hydride | 0.06 | Cyclohexane | 91 |

| Example Number | Reaction Time (hr) I[1] | Reaction Time (hr) II[2] | Reaction Temperature (°C.) | Raw Yield[3] (%) | $M_n$ | $M_w$ | Iodine Number |
|---|---|---|---|---|---|---|---|
| 15 | 24 | 0 | 200 | 78 | 606 | 796 | 61 |
| 16 | 46 | 4.0 | 200 | 70 | 1137 | 2520 | 45 |
| 17 | 30 | 0 | 200 | 76 | 595 | 730 | 30.3 |
| 18 | 30 | 1.0 | 200 | 83 | 696 | 952 | 32 |
| 19 | 24 | 1 | 200 | 81 | 880 | 1300 | 35 |
| 20 | 8 | 4 | 220 | 58 | 430 | 467 | 146 |
| 21 | 24 | 1 | 200 | 59 | 852 | 1167 | 21 |

[1] Reaction time I, total reaction time
[2] Reaction time II, reaction time prior to addition of hydrogen
[3] Based on the molar amount of the diolefin charged, prior to distillation

EXAMPLES 22-25

The various α,ω-diolefins in Table 3 were reacted by the same method as employed in Examples 1-14 and with the same apparatus. The products were refined and characterized by the methods of Examples 1-14. All other data on starting products, end products, and reaction conditions, are provided in Table 3.

TABLE 3

| Example Number | Diolefin I | Diolefin II | Molar ratio I to II | Catalyst | Concentration[1] (mol-%) |
|---|---|---|---|---|---|
| 22 | 1,7-Octadiene | 4-Vinylcyclohexene | 1/1 | Diisobutylaluminum hydride | 3.74 |
| 23 | " | " | 3/1 | Diisobutylaluminum hydride | 3.83 |
| 24 | " | 1,9-Decadiene | 1/1 | Diisobutylaluminum hydride | 3.86 |
| 25 | " | " | 1/1 | Diisobutylaluminum hydride | 3.86 |

| Example Number | Reaction Time (hr) | Reaction Temperature (°C.) | Raw Yield[2] (%) | $M_n$ | $M_w$ | Iodine Number |
|---|---|---|---|---|---|---|
| 22 | 1 | 200 | 67 | 460 | 556 | 267 |
| 23 | 2 | 200 | 71 | 611 | 896 | 256 |
| 24 | 1 | 200 | 61 | 470 | 573 | 251 |
| 25 | 2 | 200 | 71 | 584 | 731 | 242 |

[1] Based on the total amount of all materials charged
[2] Based on the molar amount of the diolefin charged, prior to distillation

EXAMPLES 26-27

The starting products in Table 4 were reacted in the presence of a monoolefin by the same method as employed in Examples 1-14 and with the same apparatus. The products were refined and characterized by the methods described in Examples 1-14. All other data on starting products, end products, and reaction conditions, are provided in Table 4.

TABLE 4

| Example Number | α,ω Diolefin | α-Olefin | Molar ratio of the olefins | Catalyst | Concentration[1] (mol-%) |
|---|---|---|---|---|---|
| 26 | 1,11-Dodecadiene | 1-Dodecene | 1/1 | Diisobutylaluminum hydride | 1.96 |
| 27 | 1,11-Dodecadiene | " | 2/1 | Diisobutylaluminum hydride | 1.96 |

| Example Number | Reaction Time (hr) | Reaction Temperature (°C.) | Raw Yield[2] (%) | $M_n$ | $M_w$ | Iodine Number |
|---|---|---|---|---|---|---|
| 26 | 20 | 180 | 81 | 561 | 605 | 248 |
| 27 | 20 | 180 | 83 | 622 | 776 | 252 |

[1] Based on the total amount of all materials charged
[2] Based on the molar amount of the diolefin charged, prior to distillation Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of manufacturing α,ω-unsaturated oligomers containing at least one methylidene group from α,ω-diolefins in the presence of a catalytic amount of organoaluminum compounds, comprising contacting α,ω-diolefins in the liquid phase, at 150°–350° C., with a catalytic amount of an organoaluminum compounds having the formula $AlX_3$ or $AlX_2H$, where X represents an aliphatic, alicyclic, or aromatic hydrocarbon group with 1–30 C atoms, and recovering said oligomer containing at least one methylidene group.

2. A method according to claim 1, wherein the α,ω-diolefins have a chain length of 5 to 30 C atoms, and is substituted other than at the terminal double bonds by alkyl, aralkyl, aryl, and cycloalkyl groups.

3. A method according to claim 1, wherein the concentration of the organoaluminum compounds is 0.1–10 mol % based on the amount of α,ω-diolefins charged.

4. A method according to claim 1, wherein the reaction is carried out in the presence or absence of an inert solvent.

5. A method according to claim 1, wherein the molecular weight of the oligomers is regulated by adding olefins having only one terminal double bond.

6. A method according to claim 1, wherein the molecular weight of the oligomers is regulated by the presence of hydrogen during the oligomerization.

7. A method according to claim 1, wherein the α,ω-diolefins have additional, interior double bonds.

8. A α,ω-unsaturated oligomers containing at least one methylidene group having the general formula:

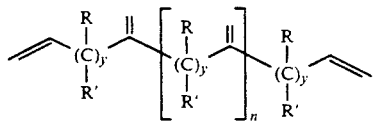

where
R and R' each independently represent hydrogen or an alkyl, aryl, aralkyl, or cycloalkyl group;
x is 1 or a number between 3 and 25;
y = x or x+2;
n is a number between 1 and 99; and
$\Sigma C_k = (x+4)(n+2)-(n+1)$ is the expression for the sum of the C-atoms in the chain.

9. A α,ω-unsaturated oligomers containing at least one methylidene group having the general formula:

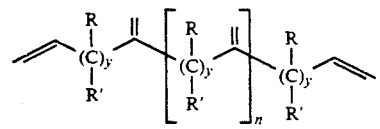

where
R and R' each independently represent hydrogen or an alkyl, aryl, aralkyl, or cycloalkyl group;
x is 1 or a number between 3 and 25;
y = x or x+2;
n is a number between 1 and 99; and
$\Sigma C_k = (x+4)(n+2)-(n+1)$ is the expression for the sum of the C-atoms in the chain;
wherein the oligomers are produced from α,ω-diolefins having the general formula:

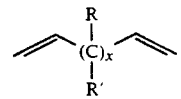

where R, R', and x have the same meanings as above, with the reaction being carried out in the presence of organoaluminum compounds as catalysts, in the liquid phase at 150°–350° C.; wherein the catalysts have general formula $AlX_3$ or $AlX_2H$, where X represents an aliphatic, alicyclic, or aromatic hydrocarbon group with 1–30 C atoms.

* * * * *